United States Patent [19]

Sussman

[11] Patent Number: 4,588,085
[45] Date of Patent: May 13, 1986

[54] STERILE AIR FEEDTHROUGH PACKAGING SYSTEM FOR TESTING HYDROCEPHALUS SHUNT VALVES

[75] Inventor: Marvin L. Sussman, Miami, Fla.

[73] Assignee: Cordis Corporation, Miami, Fla.

[21] Appl. No.: 710,439

[22] Filed: Mar. 11, 1985

[51] Int. Cl.⁴ ............................................. B65D 81/20
[52] U.S. Cl. ........................................ 206/438; 73/52;
206/461; 604/9
[58] Field of Search ..................... 3/1, 1.2; 73/49.3, 52;
128/419 P, 419 PG, 420 R, DIG. 7, DIG. 10,
DIG. 12; 206/438, 439, 484.1, 461; 604/8–10

[56] References Cited

U.S. PATENT DOCUMENTS

| | | | |
|---|---|---|---|
| 3,926,311 | 12/1975 | Laske | 206/439 |
| 3,991,768 | 11/1976 | Portnoy | 604/10 |
| 4,270,658 | 6/1981 | Schuster | 206/484.1 |
| 4,296,862 | 10/1981 | Armentrout et al. | 206/484.1 |
| 4,423,732 | 1/1984 | Tarjan et al. | 128/419 P |

Primary Examiner—William Price
Assistant Examiner—Jimmy G. Foster
Attorney, Agent, or Firm—Henry W. Collins; Thomas R. Vigil

[57] ABSTRACT

The packaging system for a sterile hydrocephalus shunt provides access to the valves of the shunt for air testing of the opening and closing pressures of the valves without compromising the sterility of the shunt. The packaging system comprises two nested plastic packs positioned around the shunt with access to the valves of the shunt being provided by an air feedthrough connector assembly which includes a bacteriostatic filter to maintain the contents of the packaging system sterile against contamination by the air used in the pressure testing of the valves. The bacteriostatic filter is impervious to bacterial contaminants but is pervious to air or gaseous sterilizing agents which may be passed therethrough.

26 Claims, 2 Drawing Figures

STERILE AIR FEEDTHROUGH PACKAGING SYSTEM FOR TESTING HYDROCEPHALUS SHUNT VALVES

BACKGROUND OF THE INVENTION

1. Field of the Invention

The present invention relates to a closed, sterile packaging system which permits air testing of the opening and closing pressures of valves of a hydrocephalus shunt received within a package while maintaining sterility of the shunt. More particularly, the invention relates to a packaging system wherein access to the shunt valves to be tested is provided by means of an air feedthrough connector having a bacteriostatic filter therein.

2. Description of the Prior Art

According to present day practices, hydrocephalus shunts are sterilized after packaging. In order to locate a shunt having valve opening and closing pressure parameters required by a specific patient, the pressures required to open and close the valves of the shunt must be ascertained prior to implantation of the shunt. Typically, to test the pressures required to open and close the valves of the shunt, the packaging must be opened, with the sterility of the shunt being destroyed. Further, if a chosen shunt does not meet the required pressure parameters, further package shunts are opened and tested until one with appropriate valve opening and closing pressure parameters is located.

This method of pressure testing of the shunt valves necessitates resterilization of shunts which are tested but not utilized due to inappropropriate pressure parameters.

By the provision of the packaging system and sterile air feedthrough connector of the present invention, the need for resterilization after testing is eliminated as will be described in greater detail hereinafter.

A packaging system which provides an electrical feedthrough connection to the interior of a "blister pack" package is disclosed in U.S. Pat. No. 4,423,732.

SUMMARY OF THE INVENTION

According to the invention there is provided a sealed, sterile packaging system having air communication means for connecting a source of pressurized air located externally of said packaging system to a device positioned in an interior compartment of the packaging system for the air pressur testing of valves of such a device comprising:

an inner package defining a first sterilizable interior compartment and having a peripheral seal which can be broken for opening said inner package:

an outer package defining a second sterilizable interior compartment that holds said inner package therein, said outer package having a peripheral seal which can be broken for opening said outer package;

means for sealing the peripheries of said inner and outer packages;

and air communication means comprising a sterile connector assembly positioned within and across a portion of the sealed periphery of the inner and outer packages, for allowing pressurized air to flow therethrough to the interior of the device in the inner package from the external source of pressurized gas without compromising the sterility of the device.

Further according to the invention there is provided a sterile connector assembly that transmits pressurized air or other gaseous substance from an externally located source to a device located within an interior compartment defined within a peripherally sealed packaging system for air pressure testing of valves of said device, said connector assembly comprising:

a cylindrical connector housing having a first end thereof located within the interior of the packaging system, a second end located exterior of the packaging system, and an intermediate portion disposed within a portion of the sealed peripheral region of the packaging system, said connector housing having a lumen extending therethrough;

a filter centrally disposed within and across said lumen of said sterile connector housing in such a manner as to allow molecules of pressurized air or other pressurized gaseous material to pass therethrough while sealing or plugging said connector housing against entry of particles which are larger than molecules of gas, such as bacterial contaminants;

sealing means for sealing said connector housing within the sealed peripheral portion of the packaging system, said sealing means being capable of maintaining said seal during periods when stress is placed on said connector housing to ensure integrity of the seal; and connecting means associated with said connector housing for connecting said first interior end of said connector housing with the interior of the device positioned within the sealed packaging system to provide a passageway through which pressurized air entering the connector assembly can be shunted into the interior of the device for air pressure testing of the valves of the device; said connecting means comprising a cannula or tube extending from said first or interior end of said connector housing to and into one end of the device packaged within the packaging system.

DESCRIPTION OF THE PREFERRED EMBODIMENT

Figure 1:
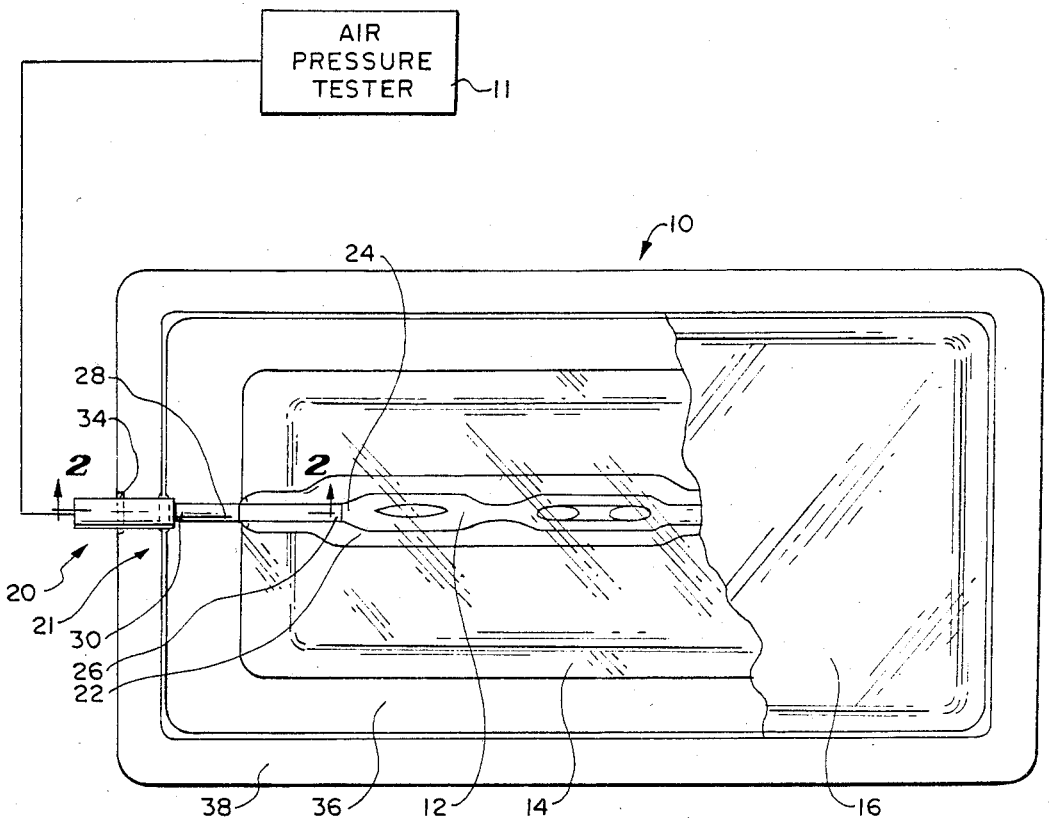
FIG. 1 is a top plan view with portions broken away of a packaging system with a sterile connector of the present invention and shows a hydrocephalus shunt received within the packaging system.

Referring now to the drawings in greater detail, there is illustrated in FIG. 1 a packaging system 10 constructed according to the teachings of the present invention. The packaging system 10 includes couplings or connectors for providing communication between an air pressure testing device 11 and a sterile hydrocephalus shunt 12 positioned within the packaging system 10 while maintaining the sterility of the shunt 12.

As shown, the system 10 comprises an inner pack 14, an outer pack 16 surrounding the inner pack 14 in a nested relationship, and a sterile connector assembly 20 which extends from the exterior environment through a peripheral marginal area 21 of both the outer and inner packs 16 and 14, respectively, and into communication with the shunt 12 positioned within the system 10 to provide a passageway for the passage of air or other gaseous substance between the exterior of the outer pack 16 and the shunt 12.

The particular hydrocephalus shunt 12 illustrated in the drawings is a Cordis-Hakim Valve System sold by Cordis Corporation of Miami, Fla. It is to be noted, however, that the packaging system 10 may be utilized with any device provided with valves, the opening and closing pressures of which are to be air tested while maintaining a sterile environment for the device.

As illustrated, the shunt 12 is positioned within a receptacle 22 molded in the inner pack 14. The receptacle 22 is molded to snugly secure the shunt 12 therein. Connected to one end 24 of the shunt 12 is one end 26 of a tubing or cannula 28 which is fabricated of a bacteriostatic material which is sold by the Dow Chemical Corporation of Michigan under the trademark Silastic. The other end 30 of the cannula 28 is in turn connected to the sterile air feedthrough connector assembly 20 which may be made of a plastic material such as polypropylene or polyethylene, or which may be made of stainless steel.

As will be described in greater detail in connection with the description of FIG. 2, the sterile air feedthrough connector assembly 20 includes a bacteriostatic filter 34 which allows passage of air or other gaseous substance therethrough but which will not allow passage of bacteria or other contaminants.

The inner pack 14 has a sealed peripheral margin 36 extending around the entire periphery thereof, and the outer pack 16 has a similar peripheral margin 38 which is sealed around the entire periphery thereof. By the provision of such a sealed pack 14 within a sealed pack 16, sterility of a device, such as the hydrocephalus shunt 12, is easily maintained.

Figure 2:
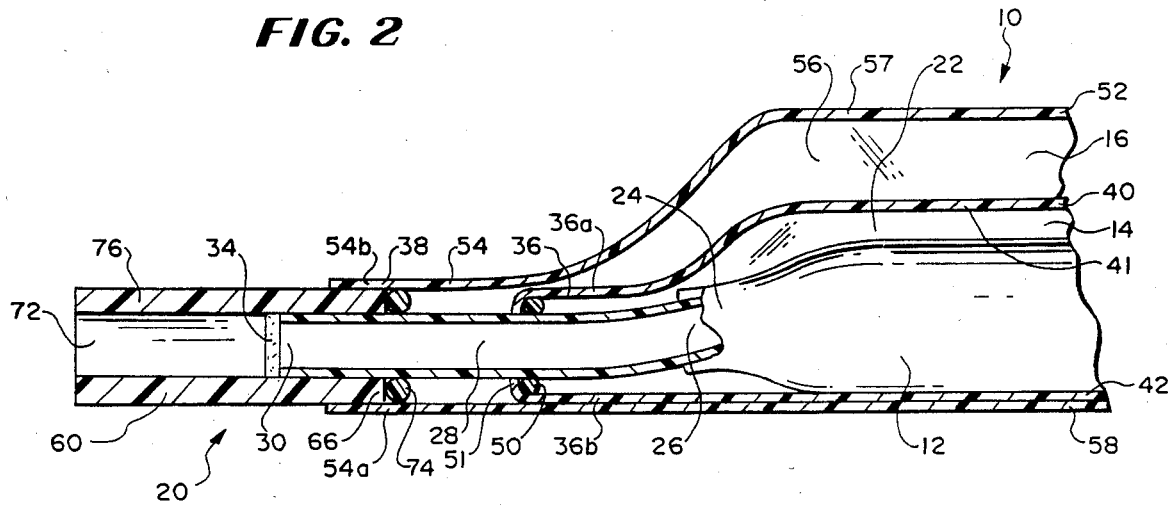
FIG. 2 is a detailed vertical sectional view through one portion of the packaging system of the present invention in the area where the sterile connector is located and is taken along line 2—2 of FIG. 1.

This type of formation of a form-fitted inner pack 14 within a form-fitted outer pack 16 is often referred to as a "double blister pack" arrangement as will be defined further in connection with the description of FIG. 2.

Turning now to FIG. 2, the inner pack 14 has an upper wall 40 which is vertically spaced in its central portion 41 from a lower, planar wall 42 to define the interior receptacle or chamber 22 therebetween. The upper wall 40 is made of a material which is impervious to the passage of bacteria or other contaminants. Further, the upper wall 40 is preferably made of a transparent material which may be readily molded by conventional vacuum-forming techniques, such a suitable material being polyvinylchloride (PVC). The transparency of the material allows for visual inspection of the content of the packaging system 10 and allows a user to read any identifying information which may be provided on the device, here the shunt 12, which may be useful in determining various parameters of the device.

The inner pack 14 preferably has its central portion 41 vertically spaced, by vacuum molding thereof, a distance which will place the central portion 41 in direct contact with a top or upper surface of the shunt 12 to form the receptacle 22 with a shape corresponding to the shape of the shunt 12 to firmly hold or secure the shunt 12 within the inner pack 14. However, peripheral marginal area 36a of the upper wall 40 of the inner pack 14 is generally planar to provide an area 36a of the upper wall 40 which can be bonded to peripheral marginal area 36b of the lower wall 42.

Such a pack 14 having an upper wall 40, the central portion 41 of which is molded to take on a shape corresponding to the shape of a device therein to firmly secure the device within the receptacle 22, is commonly referred to as a "blister" pack 14.

The bottom wall 42 of the inner pack 14 is a flat, planar structure which is substantially coextensive with upper wall 40. This bottom wall 42 is preferably formed of a film-type material which is impervious to bacteria or other contaminants but which is pervious to a gas-phase sterilizing agent, such as ethylene oxide, a commonly utilized gas-phase sterilizing agent. Further, the bottom wall 42 is provided with a coating of a suitable adhesive material which causes it to bond loosely to the bottom surface of a device placed thereon and firmly yet releasably to the planar peripheral marginal area 36a of the upper wall 40 of the inner pack 14 under the application of heat and pressure to the peripheral margin 36 of the pack 14. A suitable material for forming the bottom wall 42 is a coated polyolefin film sold under the trademark Tyvek.

Once the bottom wall 42 is bonded or joined to the upper wall 40 along its peripheral marginal area 36, a continuous peripheral seal between the walls 40 and 42 is formed which is only interrupted in the area through which the sterile air feedthrough connector assembly 20 passes. To ensure a sterile seal around the area of interruption of the peripheral margin 36 formed in the inner pack 14, a bead or ring 50 of bacteriostatic material, such as that sold under the trademark Silastic, is positioned along an inner surface of the pack 14 in the area of interruption to ensure that the sterility of the content of the pack 14 is not compromised.

During heat sealing of the inner pack 14, the Silastic melts and flows around the connector assembly 20 to form an airtight seal in the area of interruption as will be described in further detail hereinafter.

The pack 14, after having the upper wall 40 thereof molded to provide the receptacle 22 therein and having the shunt 12 positioned therein, and having the bottom wall 42 placed in position to have its peripheral marginal area 36b coextensive with the peripheral marginal area 36a of the upper wall 40, and, after placement of the cannula 28 in such a manner as to provide air communication between the valves of the shunt 12 and the air pressure testing device 11, is heat sealed to provide the airtight packaging system 10.

However, since the peripheral marginal area 36a of the upper wall 40 of the inner pack 14 cannot be heat sealed to the bottom wall 42 in the area where the cannula 28 enters the inner pack 14, to ensure a bacteriostatic closure around the peripheral margin 36 of the pack 14, a bead or ring 68 of Silastic is positioned just interior to a lip 70 formed in the peripheral margin 36 prior to the heat sealing of the upper and bottom walls 40 and 42 together. As the peripheral marginal area 36a of the upper wall 40 is heat sealed to the peripheral marginal area 36b of the bottom wall 42, this Silastic bead 68 melts and molds itself between the cannula 28 and the pack 14 to form a bacteriostatic closure which is air-tight as well.

The seal formed, as described above, around the peripheral margin 36 of the pack 14 can be broken manually, when necessary, by separating the walls 40 and 42 along the bonded peripheral margin 36 and access to the shunt 12, once the shunt 12 has been determined to provide required opening and closing valve pressure parameters, can be easily obtained to remove it from its position within the inner pack 14.

The outer pack 16 has generally the same construction as that of the inner pack 14. The pack 16 is also provided with an upper molded wall 52 which is formed of a material having the same characteristics as the upper wall 40 of the inner pack 14. The wall 52 also has a generally flat peripheral margin 54 and a receptacle 56 formed in the molded central area 57 within which the molded receptacle 22 formed in the upper wall 40 of the inner pack 14 is received.

As described, the wall 52 is configured to receive and secure the receptacle 22 of the inner pack 14 in a nested relation with respect to the receptacle 56 of the outer pack 16.

A bottom wall 58 of the outer pack 16 is formed of the same material as the bottom wall 42 of the inner pack 14. The bottom wall 58 of the outer pack 16 is also sealed around its peripheral marginal area 54a to planar peripheral marginal area 54b of the upper wall 52. The peripheral seal formed along the margin 54 between the upper wall 50 and bottom wall 58 of the outer pack 16 blocks the passage of bacteria or other contaminants from the exterior of the packaging system 10 to the interior of the receptacle 56 formed in the outer pack 16.

To provide access to the hydrocephalus shunt 12 which is positioned within the receptacle 22 of the inner pack 14 for the air testing of valve opening and closing pressures, the sterile connector assembly 20 is provided.

The sterile connector assembly 20, as shown, comprises a connector housing 60, the bacteriostatic filter 34 within the connector housing 60 and the cannula 28 extending from one end of the connector housing 60.

As illustrated, one end 65 of the cannula 28 exits an interior end 66 of the connector housing 60 and extends inwardly toward and into connection with the shunt 12. To reach the shunt 12, the cannula 28 must pass through the sealed peripheral margin 36 of the inner pack 14. The connection of the cannula 28 with the shunt 12 is made in such a manner as to ensure that air passing through the cannula 64 and into the shunt 12 will not leak into the interior compartment 22 of the pack 14 from the area of connection so that an incorrect reading of valve opening and closing pressure is not obtained.

The end 30 of the cannula 28, is connected by appropriate means to inner end 66 of the connector housing 60 to form an air-tight, and thus bacteriostatic, seal. In this respect, as shown, the cannula 28 is received in a throughbore 72 provided within the connector housing 60. Further, the connector housing 60 is secured within the peripheral margin 54 of the outer pack 16.

Once again, to ensure the sterile integrity of the seal formed along the peripheral margin 54 of the outer pack 16 in the area where the connector housing 60 exits the outer pack 16, another bead 74 of Silastic is positioned internally of the inner end 66 of the connector housing 60 and forms a molded seal between the upper wall 52 of the outer pack 16 and the cannula 28 as well as forming a seal between the bottom wall 58 of the pack 16 and the cannula 28.

In this respect, also, once the peripheral margin 54 of the outer pack 16 is heat treated to seal same, the Silastic bead 74 will melt and form an air-tight, bacteriostatic seal for the outer pack 16.

The content of the packaging system 10 can then be sterilized by passing a gas-phase sterilizing agent through the bottom walls 42 and 58, under pressure, with the sterility of the interior of the packs 14 and 16 being maintainable for an indefinite period of time.

Further, located approximately halfway between the ends of the connector housing 60 and positioned across the lumen 72 of the connector assembly 20 is the filter 34. This filter 34 is formed of a material similar to the material from which the bottom walls 42 and 58 of the inner and outer packs 14 and 16, respectively, are formed. This material is preferably a bacteriostatic film sold under the trademark Tyvek.

The connector 60 has an outer end 76 which, as shown in FIG. 1, is adapted to receive a coupling (not shown) of an air pressure testing device 11. The filter 34 is provided in an area of the connector housing 60 so that it is positioned between the coupling (not shown) of the air testing device 11 in the outer end 76 of the housing 60 which is in turn connected to the hydrocephalus shunt 12.

In testing the opening and closing pressures of the valves of the hydrocephalus shunt 12, the coupling (not shown) of the air pressure testing device 11 is secured to the outer end 76 of the connector housing 60. Air is then forced by the air pressure testing device 11 into the connector end 76, through the filter 34, into and through the cannula 28, and into the hydrocephalus shunt 12. By taking appropriate readings of the pressures required to open and close the valves within the shunt 12, a physician will be provided with the parameters of the valves which are necessary to determine whether the shunt 12 being tested is appropriate for use in a patient having required opening and closing pressure parameters.

If the shunt 12 has the appropriate parameters, after testing, the packaging system 10 may be opened, the shunt 12 removed and utilized within the patient. However, as is oftentimes the case, several hydrocephalus shunts 12 need to be tested until a physician or other user locates a shunt 12 with appropriate valve opening and closing pressures. It is in such instances, that the sterile connector assembly 20 of the present invention becomes an invaluable tool. In this respect, since the sterile connector assembly 20 is provided with the sterile bacteriostatic filter 34, the air entering the shunt 12 for the valve opening and closing pressure testing is sterile, and therefore, the sterility of the shunt is maintained. Since the sterility of the shunt 12 is maintained, the necessity for re-sterilization is obviated.

In other words, since the sterility of the shunt 12 has not been compromised by the air pressure testing, due to the positioning of the bacteriostatic filter within the connector which sterilizes the air being fed into the shunt 12, the necessity for re-sterilizing every shunt 12 which is not utilizable due to undesired or inappropriate valve opening and closing pressure parameters, those shunts 12 that are put aside and not utilized, need not be resterilized, saving in both time and manpower.

Further, if for some reason resterilization is necessary, by providing the packaging system 10 with bottom walls 42 and 58 which are also made of the film sold under the trademark Tyvek, resterilization of the shunt 12 may be accomplished without the necessity of removing the shunt 12 from the packaging system 10. In this respect, since the bottom walls 42 and 58 of the system 10 are made of Tyvek, a film that is pervious to gaseous substances, such as ethylene chloride, a gaseous sterilizing agent which is often utilized in sterilizing hydrocephalus shunts, the system 10 may be placed in appropriate contact with such gaseous substance which will permeate through the bottom walls 42 and 58 of the system 10 and resterilize the shunt 12 located within the system 10.

As described above, the packaging system 10 with sterile connector assembly 20 thereof has a number of advantages, some of which have been described above and others of which are inherent in the invention. For example, since a double "blister pack" is used, the outer pack 16 can be opened to transfer the inner pack 14 with the hydrocephalus shunt 12 therein to the sterile field during a surgical procedure of implantation. If the implant of the valve is aborted, at this point, the inner pack, while still positioned around the shunt 12, maintains the shunt 12 in a sterile condition.

Also, modifications can be made to the packaging system 10 and sterile connector assembly 20 without departing from the teachings of the present invention. Accordingly, the scope of the invention is only to be limited as necessitated by the accompanying claims.

I claim:

1. A sealed, sterile packaging system having air communication means for connecting a source of pressurized air located externally of said packaging system to a device positioned in an interior compartment of the packaging system for the air pressure testing of valves of such a device comprising:
an inner package defining a first sterilizable interior compartment and having a peripheral seal which can be broken for opening said inner package;
an outer package defining a second sterilizable interior compartment that holds said inner package therein, said outer package having a peripheral seal which can be broken for opening said outer package;
means for sealing the peripheries of said inner and outer packages;
and air communication means comprising a sterile connector assembly positioned within and across a portion of the sealed periphery of the inner and outer packages, for allowing pressurized air to flow therethrough to the interior of the device in the inner package from the external source of pressurized gas without compromising the sterility of the device.

2. The packaging system of claim 1 wherein said connector assembly comprises a cylindrical connector housing, one end of which is capable of being connected to the interior of the device within the first interior compartment of said packaging system and the other end of which is capable of receiving a connector of an air pressure testing device thereon.

3. The packaging system of claim 2 wherein said connector housing has a bacteriostatic filter extending acrosss a lumen thereof.

4. The packaging system of claim 3 wherein said bacteriostatic filter is made of a coated polyolefin.

5. The packaging system of claim 4 wherein said coated polyolefin is air-permeable.

6. The packaging system of claim 2 wherein said connector housing is made of a bacteriostatic material.

7. The packaging system of claim 6 wherein said connector housing is made of steel.

8. The packaging system of claim 6 wherein said connector housing is made of polyethylene.

9. The packaging system of claim 1 wherein said inner and outer packages are substantially the same and comprise a planar bottom wall and a molded upper wall.

10. The packaging system of claim 9 wherein the upper wall of each package is made of polyvinylchloride.

11. The packaging system of claim 9 wherein the bottom wall of each package is made of a coated polyolefin.

12. The packaging system of claim 11 wherein said coated polyolefin is air-permeable.

13. The packaging system of claim 11 wherein said connector housing is made of polyvinylchloride.

14. The packaging system of claim 1 wherein said means for sealing the peripheries of said inner and outer packs comprise a heat activated sealant.

15. The packaging system of claim 14 wherein said sealing means further include a bead of silastic positioned around the area of the periphery of each package through which said connector assembly passes.

16. The packaging system of claim 9 wherein said upper molded wall and planar bottom wall of each package are formed to be capable of being separated from each other by pulling them apart from a periphery thereof.

17. A sterile connector assembly that transmits pressurized air or other gaseous substance from an externally located source to a device located within an interior compartment defined within a peripherally sealed packaging system for air pressure testing of valves of the device, said connector assembly comprising:
a cylindrical connector housing having a first end thereof located within the interior of the packaging system, a second end located exterior of the packaging system, and an intermediate portion disposed within a portion of the sealed peripheral region of the packaging system, said connector housing having a lumen extending therethrough;
a filter centrally disposed within and across said lumen of said sterile connector housing in such a manner as to allow molecules of pressurized air or other pressurized gaseous material to pass therethrough while sealing or plugging said connector housing against entry of particles which are larger than molecules of gas, such as bacterial contaminants;
sealing means for sealing said connector housing within the sealed peripheral portion of the packaging system, said sealing means being capable of maintaining said seal during periods when stress is placed on said connector housing to ensure integrity of the seal; and
connecting means associated with said connector housing for connecting said first interior end of said connector housing with the interior of the device positioned within the sealed packaging system to provide a passageway through which pressurized air entering the connector assembly can be shunted into the interior of the device for air pressure testing of the valves of the device; said connecting means comprising a cannula or tube extending from said first or interior end of said connector housing to and into one end of the device packaged within the packaging system.

18. The assembly of claim 17 wherein said connector housing is made of a bacteriostatic material.

19. The connector assembly of claim 18 wherein said connector housing is made of steel.

20. The connector assembly of claim 19 wherein said connector housing is made of polyvinylchloride.

21. The connector assembly of claim 18 wherein said connector housing is made of polyethylene.

22. The connector assembly of claim 17 wherein said bacteriostatic filter is made of a coated polyolefin.

23. The connector assembly of claim 22 wherein said coated polyolefin is air-permeable.

24. The assembly of claim 17 wherein said cannula is made of a suitable plastic material.

25. The connector of claim 24 wherein said plastic material is a bacteriostatic silicone rubber.

26. The connector or claim 17 wherein the connection of said cannula to said device is air-tight.

* * * * *